United States Patent
Möckli

(10) Patent No.: US 7,189,268 B2
(45) Date of Patent: *Mar. 13, 2007

(54) METHOD OF DYEING KERATIN-CONTAINING FIBRES

(75) Inventor: Peter Möckli, Schönenbuch (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/235,912

(22) Filed: Sep. 27, 2005

(65) Prior Publication Data

US 2006/0026776 A1 Feb. 9, 2006

Related U.S. Application Data

(63) Continuation of application No. 10/398,825, filed as application No. PCT/EP01/11706 on Oct. 10, 2001, now abandoned.

(30) Foreign Application Priority Data

Oct. 12, 2000 (CH) .................................. 2006/00

(51) Int. Cl.
*A61K 7/13* (2006.01)
(52) U.S. Cl. ...................... 8/405; 8/466; 8/570; 8/573; 8/437; 132/202; 132/208; 548/300
(58) Field of Classification Search ............. 8/405, 8/437, 466, 570, 573; 132/202, 208; 548/300
See application file for complete search history.

(56) References Cited

U.S. PATENT DOCUMENTS

| 3,649,162 | A | * | 3/1972 | James | 8/539 |
| 5,708,151 | A | | 1/1998 | Möckli | 534/608 |
| 5,879,412 | A | * | 3/1999 | Rondeau et al. | 8/411 |
| 6,436,153 | B2 | * | 8/2002 | Rondeau | 8/426 |
| 6,762,287 | B2 | * | 7/2004 | Mockli | 534/607 |

FOREIGN PATENT DOCUMENTS

| EP | 885046 | * | 12/1961 |
| EP | 0 714 954 A2 | * | 6/1996 |
| EP | 0714954 | | 6/1996 |
| EP | 0 962 219 A2 | * | 8/1999 |
| EP | 0962219 | | 8/1999 |
| FR | 2779055 | | 12/1999 |
| WO | 95/01772 | | 1/1995 |
| WO | 99/40895 | | 8/1999 |

OTHER PUBLICATIONS

STIC Search Report dated Oct. 19, 2006.*

* cited by examiner

*Primary Examiner*—Eisa Elhilo
(74) *Attorney, Agent, or Firm*—Mervin G. Wood; Kevin T. Mansfield

(57) ABSTRACT

A method of dyeing keratin-containing fibres, which comprises using a dye of formula

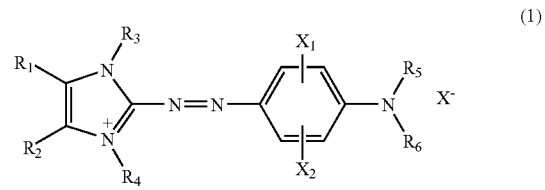

(1)

wherein
$R_1$ and $R_2$ are each independently of the other hydrogen, $C_1$–$C_4$alkyl, halogen or nitro,
$R_3$ and $R_4$ are each independently of the other unsubstituted $C_1$–$C_4$alkyl or $C_1$–$C_4$alkyl substituted by OH, $C_1$–$C_4$alkoxy, halogen, CN or by phenyl,
$X_1$ and $X_2$ are each independently of the other hydrogen, $C_1$–$C_4$alkyl, $C_1$–$C_4$alkoxy or halogen,
$R_5$ is hydrogen or $C_1$–$C_4$alkyl,
$R_6$ is $C_5$–$C_{12}$alkyl or $C_5$–$C_8$cycloalkyl each unsubstituted or substituted by OH, $C_1$–$C_4$alkoxy, halogen, CN or phenyl, or $R_6$ is $C_1$–$C_4$alkyl substituted by phenyl or by $C_5$–$C_8$cycloalkyl, or wherein $R_5$ and $R_6$ together with the nitrogen atom linking them form a piperazine ring, which is substituted, at the nitrogen atom that is not bonded to the phenyl group, by $C_1$–$C_8$-alkyl or phenyl, or which is quaternised at that nitrogen atom by two such groups, the $C_1$–$C_8$-alkyl radicals and phenyl mentioned as substituents of the nitrogen atom of the piperazine ring being unsubstituted or substituted by OH, $C_1$–$C_4$alkoxy, halogen, CN or phenyl, and wherein $X^-$ is an anion.

9 Claims, No Drawings

METHOD OF DYEING KERATIN-CONTAINING FIBRES

This application is a continuation of application Ser. No. 10/398,825, abandoned, which is the National Stage of International Application PCT/EP01/11706, filed Oct. 10, 2001.

The present invention relates to a method of dyeing keratin-containing fibres, especially human hair, using cationic imidazole azo dyes.

Cationic imidazole azo dyes and the use thereof for dyeing hair are already known, for example, from WO 95/01772 and EP-A-714 954. Such dyes are especially suitable for dyeing undamaged hair, since they are capable of penetrating into the hair shaft relatively easily on account of their low molecular weight. They also exhibit good fastness to washing on undamaged hair, but are washed out of severely damaged (bleached) hair relatively easily. There is accordingly a need for further direct hair dyes having improved properties that are in addition storage-stable in aqueous solution at alkaline pH values.

It has now been found that the dyes of formula (1) hereinbelow are especially suitable for dyeing hair and that the dyeings obtained are distinguished especially by good fastness to washing properties.

The present invention accordingly relates to a method of dyeing keratin-containing fibres, which comprises using a dye of formula

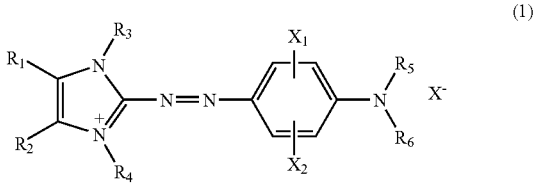

(1)

wherein $R_1$ and $R_2$ are each independently of the other hydrogen, $C_1$–$C_4$alkyl, halogen or nitro, $R_3$ and $R_4$ are each independently of the other unsubstituted $C_1$–$C_4$alkyl or $C_1$–$C_4$alkyl substituted by OH, $C_1$–$C_4$alkoxy, halogen, CN or by phenyl, $X_1$ and $X_2$ are each independently of the other hydrogen, $C_1$–$C_4$alkyl, $C_1$–$C_4$alkoxy or halogen, $R_5$ is hydrogen or $C_1$–$C_4$alkyl, $R_6$ is $C_5$–$C_{12}$alkyl or $C_5$–$C_8$cycloalkyl each unsubstituted or substituted by OH, $C_1$–$C_4$alkoxy, halogen, CN or phenyl, or $R_6$ is $C_1$–$C_4$alkyl substituted by phenyl or by $C_5$–$C_8$cycloalkyl, or wherein $R_5$ and $R_6$ together with the nitrogen atom linking them form a piperazine ring, which is substituted, at the nitrogen atom that is not bonded to the phenyl group, by $C_1$–$C_8$-alkyl or phenyl, or which is quaternised at that nitrogen atom by two such groups, the $C_1$–$C_8$-alkyl radicals and phenyl mentioned as substituents of the nitrogen atom of the piperazine ring being unsubstituted or substituted by OH, $C_1$–$C_4$alkoxy, halogen, CN or phenyl, and wherein $X^-$ is an anion.

In accordance with the invention, alkyl radicals are to be understood generally as straight-chain or branched alkyl radicals, for example methyl, ethyl, n- and iso-propyl and n-, sec- and tert-butyl.

The alkyl radicals and also the cycloalkyl groups may be mono- or poly-substituted, for example by hydroxy, carboxy, halogen, cyano or $C_1$–$C_4$alkoxy.

The alkoxy radicals may contain from 1 to 12 carbon atoms, preferably from 1 to 4 carbon atoms. They are, for example, methoxy, ethoxy, propoxy, isopropoxy, n-butoxy, isobutoxy, tert-butoxy, n-pentyloxy or n-hexyloxy. The alkoxy groups, too, may be substituted, for example by the radicals mentioned as possible substituents for the alkyl groups, especially by hydroxy or $C_1$–$C_4$alkoxy.

Suitable anions $X^-$ include both inorganic and organic anions, for example halide, such as chloride, bromide or iodide, sulfate, hydrogen sulfate, methyl sulfate, boron tetrafluoride, aminosulfonate, perchlorate, carbonate, bicarbonate, phosphate, nitrate, benzenesulfonate, formate, acetate, propionate, lactate, and complex anions, such as the anion of a zinc chloride double salt.

The anion is generally predetermined by the preparation process. Preferably, chlorides, hydrogen sulfates, sulfates, methosulfates, phosphates, formates, lactates or acetates are present.

Halogen is to be understood as fluorine, bromine or iodine or, especially, chlorine.

Each of $R_1$ and $R_2$ is preferably methyl and especially hydrogen.

Each of $R_3$ and $R_4$ is preferably ethyl, hydroxyethyl or especially methyl.

Each of $X_1$ and $X_2$ is preferably methoxy, methyl, chlorine or especially hydrogen.

$R_5$ is preferably hydrogen, methyl or ethyl, especially hydrogen or methyl. Preferably, $R_5$ is hydrogen.

$C_5$–$C_{12}$Alkyl radicals $R_6$ are preferably corresponding unsubstituted alkyl radicals, especially $C_5$–$C_8$alkyl radicals and preferably $C_6$–$C_8$alkyl radicals.

$C_5$–$C_8$Cycloalkyl radicals $R_6$ are preferably corresponding unsubstituted cycloalkyl radicals, especially cyclohexyl radicals.

Phenyl-substituted or $C_5$–$C_8$cycloalkyl-substituted $C_1$–$C_4$alkyl $R_6$ is preferably phenyl-substituted or cyclohexyl-substituted $C_1$–$C_4$alkyl, especially phenyl-substituted $C_1$–$C_4$alkyl.

As piperazine rings formed by $R_5$ and $R_6$ together with the nitrogen atom linking them, preference is given to those which are substituted, at the nitrogen atom that is not bonded to the phenyl group, by $C_1$–$C_8$alkyl, especially $C_1$–$C_4$alkyl, or by phenyl.

$R_6$ is especially preferably $C_5$–$C_8$alkyl;
or cyclohexyl;
or phenyl-substituted $C_1$–$C_4$alkyl, like benzyl;
or $R_5$ and $R_6$ together with the nitrogen atom linking them form a piperazine ring which is substituted, at the nitrogen atom that is not bonded to the phenyl group, by $C_1$–$C_4$alkyl or phenyl.

Especially preferred dyes used according to the invention are those of formula

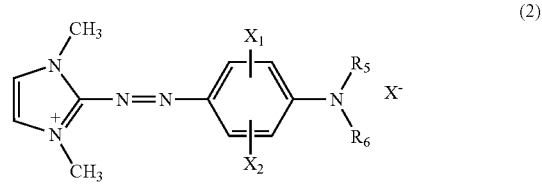

(2)

wherein $X_1$ and $X_2$ are each independently of the other hydrogen, methyl or methoxy, $R_5$ is hydrogen, $R_6$ is benzyl, $C_6$–$C_8$alkyl or cyclohexyl, or wherein $R_5$ and $R_6$ together with the nitrogen atom linking them form a piperazine ring, which is substituted, at the nitrogen atom that is not bonded to the phenyl ring, by $C_1$–$C_4$alkyl or phenyl, and $X^-$ is an anion.

More especially preferred are dyes of formula (2) wherein $R_8$ is benzyl, $C_6$–$C_8$alkyl or cyclohexyl.

Some of the dyes of the formula (1) are known, e.g. from EP-A-714 954.

Novel are the compounds of formula

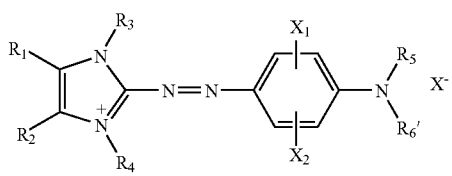

(3)

wherein $R_1$ and $R_2$ are each independently of the other hydrogen, $C_1$–$C_4$alkyl, halogen or nitro, $R_3$ and R4 are each independently of the other unsubstituted $C_1$–$C_4$alkyl or $C_1$–$C_4$alkyl substituted by OH, $C_1$–$C_4$alkoxy, halogen, CN or by phenyl, $X_1$ and $X_2$ are each independently of the other hydrogen, $C_1$–$C_4$alkyl, $C_1$–$C_4$alkoxy or halogen, $R_5$ is hydrogen or $C_1$–$C_4$alkyl, $R_6$' is $C_5$–$C_{12}$alkyl; $C_5$–$C_8$cycloalkyl or phenyl-substituted $C_1$–$C_4$alkyl; or wherein $R_5$ and $R_6$ together with the nitrogen atom linking them form a piperazine ring, which is substituted, at the nitrogen atom that is not bonded to the phenyl group, by $C_1$–$C_4$-alkyl or phenyl, and $X^-$ is an anion.

In respect of the substituents, the preferences indicated above apply, and in respect of $R_6$' the preferences indicated above for $R_6$ apply.

$R_5$' is especially preferably $C_6$–$C_8$alkyl, phenyl-substituted $C_1$–$C_8$alkyl or $C_5$–$C_8$cycloalkyl.

The invention relates also to the compounds of formula (3).

The dyes of formula (1) can be prepared according to methods known per se (see e.g. EP-A-714 954).

The dyes of formula (1) can be obtained, for example, by reacting a compound of formula

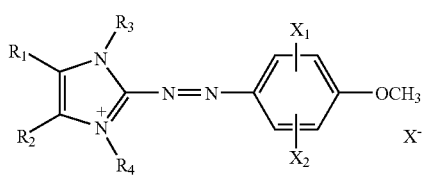

(4)

with an amine of formula

 (5)

wherein the substituents have the definitions and preferred meanings indicated above. Alternatively, it is also possible to use as compounds of formula (4) those compounds which, instead of the methoxy group indicated, contain halogen, e.g. chlorine, or $C_2$–$C_4$alkoxy. The compounds of formulae (4) and (5) are known or can be prepared in a manner known perse. For example, the compounds of formula (4) can be obtained by diazotising 4-alkoxyanilines, coupling the product with an imidazole and then carrying out alkylation and quaternisation.

The reaction of a compound of formula (4) with an amine of formula (5) can be carried out, for example, at a temperature of about from 40 to 100° C., preferably from 40 to 70° C, optionally under pressure and/or in an inert gas atmosphere, and in an inert solvent, e.g. in water or especially aliphatic alcohols, e.g. $C_1$–$C_8$alcohols, such as methanol, ethanol or especially isopropanol. It is also possible to carry out the reaction in aprotic polar solvents, such as dimethylformamide or dimethyl sulfoxide. In the case of amines that are liquid under the reaction conditions, it is possible, if desired, to dispense with a solvent.

The invention relates also to compositions for dyeing keratin-containing material that comprise such dyes.

The compounds of formula (1) are present in the compositions according to the invention preferably in an amount of from 0.001% to 5%, especially from 0.01% to 1%, based on the total dyeing composition.

The diversity of shades and the colour fastness of the dyes of formula (1) used in accordance with the invention can be increased by combination with other dyes used in the field of hair-dyeing compositions. They can be combined very readily both with oxidation dyes and with direct dyes, it being possible for the latter to be of cationic nature or also uncharged. Only in the case of anionic direct dyes is a certain degree of caution required, since precipitation may possibly occur in the formulation.

In all dyeing compositions, it is also possible for a plurality of different dyeing substances to be used together; likewise, it is possible for a plurality of different oxidation dye precursors from the group of the developer and coupler compounds to be used together, for example aromatic compounds having a primary or secondary amino group, nitrogen-containing heterocycles, aromatic hydroxy compounds or amino acids, as described, for example, in German Patent Application 197 17 224.5.

The dyes of formula (1) according to the invention produce colour shades in the range from yellowish-red to bluish-red, and the fastness properties are excellent. Attention is drawn to the property thereof that enables hair that has already been dyed a dark colour still to be distinctly altered in shade. In addition, the dyes are distinguished by a good storage stability also at Alkaline pH values, e.g. pH 9.5.

For dyeing hair there are preferably used dyes of formula (1) in admixture with one or more further cationic dyes, for example in mixtures comprising a dye of formula (1) and at least one of the dyes described in WO 95/01772. For example one, two, three or even more dyes from WO 95/01772 may be used. There may be mentioned as examples of such dyes the yellow dye according to Example 1, the red dye according to Example 4 and the orange dye according to Example 46 of WO 95/01772. Especially suitable are dye mixtures comprising a dye of formula (1) and the yellow dye according to Example 1 and/or the red dye according to Example 4 and/or the orange dye according to Example 46 of WO 95/01772.

In a further embodiment, for the purpose of further modification of colour shades the dyeing compositions according to the invention comprise, in addition to the dyes of formula (1) according to the invention, customary direct dyes, for example from the group of the nitroanilines, nitrophenylenediamines, nitroaminophenols, anthraquinones, indophenols, phenazines, phenothiazines, methines or the compounds known as Arianors, such as, for example, the compounds known by the international names or trade names HC Yellow 2, HC Yellow 4, HC Yellow 6, Basic Yellow 57, Basic Yellow 9, Disperse Orange 3, HC Red 3, HC Red BN, Basic Red 76, Basic Red 2, Basic Violet 14, Basic Blue 3, Basic Blue 6, Basic Blue 7, Basic Blue 9, Basic Blue 12, Basic Blue 26, HC Blue 2, HC Blue 7, HC Blue 12, Disperse Blue 3, Basic Blue 99, HC Violet 1, Disperse Violet 1, Disperse Violet 4, Disperse Black 9, Basic Brown 16 und Basic Brown 17, and also picramic acid, 2-amino-6-chloro-4-nitrophenol, 4-amino-2-nitrodiphenylamine-2'-carboxylic acid, 6-nitro-1,2,3,4-tetrahydroquinoxaline, 4-N-ethyl-1,4-bis(2'-hydroxyethylamino)-2-nitrobenzene hydrochloride and 1-methyl-3-nitro-4-(2'-hydroxyethyl)-aminobenzene.

Also very suitable for combination with the dyes according to the invention are cationised nitroaniline and anthraquinone dyes, for example those described in the following patent specifications: U.S. Pat. No. 5,298,029, especially in column 2, line 33 to column 5, line 38; U.S. Pat. No. 5,360,930, especially in column 2, line 38 to column 5, line 49; U.S. Pat. No. 5,169,403, especially in column 2, line 30 to column 5, line 38; U.S. Pat. No. 5,256,823, especially in column 4, line 23 to column 5, line 15; U.S. Pat. No. 5,135,543, especially in column 4, line 24 to column 5, line 16; EP-A-818 193, especially on page 2, line 40 to page 3, line 26; U.S. Pat. No. 5,486,629, especially in column 2, line 34 to column 5, line 29; and EP-A-758 547, especially on page 7, line 48 to page 8, line 19.

Also, cationic azo dyes, e.g. according to GB-A-2 319 776, as well as the oxazine dyes described in DE-A-299 12 327 and mixtures thereof with the other direct dyes mentioned therein, are likewise very suitable for combination.

The compositions of the invention according to this embodiment contain the dyes preferably in an amount of from 0.01 to 5% by weight, based on the total dyeing composition.

In addition, the dyeing compositions according to the invention may also comprise naturally occurring dyes, such as, for example, henna red, henna neutral, henna black, camomile blossom, sandalwood, black tea, Rhamnus frangula bark, sage, campeche wood, madder root, catechu, sedre and alkanet root. Such dyeing methods are described, for example, in EP-A-404 868, especially page 3, line 55 to page 4, line 9.

In respect of further customary dye components, reference is made expressly to the series "Dermatology", edited by Ch. Culnan, H. Maibach, Verlag Marcel Dekker Inc., New York, Basle, 1986, Vol. 7, Ch. Zviak, The Science of Hair Care, chapter 7, pages 248–250 (direct dyes), and chapter 8, pages 264–267 (oxidation dyes), and to "Europäisches Inventar der Kosmetikrohstoffe", 1996, published by The European Commission, obtainable in diskette form from the Bundesverband der deutschen Industrie-und Handelsunternehmen für Arzneimittel, Reformwaren und Körperpflegemittel e.V., Mannheim.

It is not necessary for the oxidation dye precursors, where present, or for the dyes each to be single compounds, but rather there may in addition be present in the dyeing compositions according to the invention, in lesser amounts, further components predetermined by the preparation processes for the individual dyes, provided such components do not have an adverse effect on the dyeing result or do not need to be excluded for other reasons, for example on toxicological grounds.

The dyes of formula (1) according to the invention may also readily be used in combination with other dyes and/or adjuvants used in the colouring of hair, for example with oxidising agents to achieve lightened colouration, as described in WO 97/20545, especially page 9, lines 5 to 9, oxidising agents in the form of permanent-wave fixing solution, as described in DE-A-19 713 698, especially page 4, lines 52 to 55, or EP-A-1 062 940, especially page 6, lines 41 to 47, (and in the equivalent WO 99/40895), oxidation dyeing compositions, as described in EP-A-850 636, especially page 5, line 41 to page 7, line 52, EP-A-850 637, especially page 6, line 50 to page 8, line 44, EP-A-850 638, especially page 7, line 20 to page 9, line 26, and EP-A-852 135, especially page 4, line 54 to page 6, line 53, oxidation dyeing compositions with cationic couplers, as described in WO 99/48856, especially page 9, line 16 to page 13, line 8, and WO 99/48875, especially page 11, line 20 to page 12, line 13, oxidation dyes in the presence of oxidoreductase enzyme, as described in WO 99/17730, especially page 4, line 11 to page 13, line 28, and WO 99/36034, especially pages 3 to 15, autooxidisable oxidation dyes, as described in WO 99/20234, especially page 26, line 16 to page 28, line 15, or nitrobenzene derivatives, as described in WO 99/20235, especially page 26, line 7 to page 30, line 15, polyols or polyethers, as described in EP-A-962 219, especially page 27, lines 14 to 38, thickening polymers, as described in EP-A-970 684, especially page 48, line 16 to page 51, line 4, sugar-containing polymers, as described in EP-A-970 687, especially page 28, line 17 to page 29, line 23, quaternary ammonium salts, as described in WO 00/10517, especially page 44, line 16 to page 46, line 23, anionic surfactants, as described in WO 00/10518, especially page 45, line 11 to page 48, line 3, non-ionic surfactants, as described in WO 00/10519, especially page 45, line 11 to page 50, line 12, or silicones, as described in WO 00/12057, especially page 45, line 9 to page 55, line 2.

The dyeing compositions according to the invention produce intense dyeings even at physiologically tolerable temperatures of less than 45° C. They are accordingly suitable especially for dyeing human hair. For use on human hair, the dyeing compositions can usually be incorporated into an aqueous cosmetic carrier. Suitable aqueous cosmetic carriers include, for example, creams, emulsions, gels and also surfactant-containing foaming solutions, e.g. shampoos or other preparations, that are suitable for use on keratin-containing fibres. Such forms of use are described in detail in Research Disclosure 42448 (August 1999). If necessary, it is also possible to incorporate the dyeing compositions into anhydrous carriers, as described, for example, in U.S. Pat. No. 3,369,970, especially column 1, line 70 to column 3, line 55. The dyeing compositions according to the invention are also excellently suitable for the dyeing method described in DE-A-3 829 870 using a dyeing comb or a dyeing brush.

The dyeing compositions according to the invention may furthermore comprise any active ingredient, additive or adjuvant known for such preparations. The dyeing compositions in many cases comprise at least one surfactant, there being suitable in principle anionic and also zwitterionic, ampholytic, non-ionic and cationic surfactants. In many cases, however, it has proved advantageous to select the surfactants from anionic, zwitterionic and non-ionic surfactants.

Anionic surfactants suitable for use in the preparations according to the invention include any anionic surface-active substance that is suitable for use on the human body. Such a substance is characterised by an anionic group that imparts water solubility, for example a carboxylate, sulfate, sulfonate or phosphate group, and a lipophilic alkyl group having approximately from 10 to 22 carbon atoms. In addition, glycol or polyglycol ether groups, ester, ether and amide groups and also hydroxy groups may be present in the molecule. The following are examples of suitable anionic surfactants, each in the form of sodium, potassium or ammonium salts or mono-, di- or tri-alkanolammonium salts having 2 or 3 carbon atoms in the alkanol group:

linear fatty acids having from 10 to 22 carbon atoms (soaps), ether carboxylic acids of formula $R-O-(CH_2-CH_2-O)_x-CH_2-COOH$, in which R is a linear alkyl group having from 10 to 22 carbon atoms and x=0 or from 1 to 16, acyl sarcosides having from 10 to 18 carbon atoms in the acyl group, acyl taurides having from 10 to 18 carbon atoms in the acyl group, acyl isothionates having from 10 to 18 carbon atoms in the acyl group, sulfosuccinic acid mono- and di-alkyl esters having from 8 to 18 carbon atoms in the alkyl group and sulfosuccinic acid monoalkylpolyoxyethyl esters having from 8 to 18 carbon atoms in the alkyl group and from 1 to 6 oxyethyl groups, linear alkanesulfonates having from 12 to 18 carbon atoms, linear α-olefin sulfonates having from 12 to 18 carbon atoms, α-sulfo fatty acid methyl esters of fatty acids having from 12 to 18 carbon atoms, alkyl sulfates and alkyl polyglycol ether sulfates of formula $R'-O(CH_2-CH_2-O)_x-SO_3H$, in which R' is a preferably linear alkyl group having from 10 to 18 carbon atoms and x'=0 or from 1 to 12, mixtures of surface-active hydroxysulfonates according to DE-A-3 725 030, sulfated hydroxyalkylpolyethylene and/or hydroxyalkylenepropylene glycol ethers according to DE-A-3 723 354, sulfonates of unsaturated fatty acids having from 12 to 24 carbon atoms and from 1 to 6 double bonds according to DE-A-3 926 344, esters of tartaric acid and citric acid with alcohols that are addition products of approximately from 2 to 15 molecules of ethylene oxide and/or propylene oxide with fatty alcohols having from 8 to 22 carbon atoms.

Preferred anionic surfactants are alkyl sulfates, alkyl polyglycol ether sulfates and ether carboxylic acids having from 10 to 18 carbon atoms in the alkyl group and up to 12 glycol ether groups in the molecule, and also especially salts of saturated and especially unsaturated $C_8-C_{22}$ carboxylic acids, such as oleic acid, stearic acid, isostearic acid and palmitic acid.

The term "zwitterionic surfactants" denotes surface-active compounds that carry at least one quaternary ammonium group and at least one $-COO^{(-)}$ or $-SO_3^{(-)}$ group in the molecule. Zwitterionic surfactants that are especially suitable are the so-called betaines, such as the N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethyl-imidazolines having from 8 to 18 carbon atoms in the alkyl or acyl group and also cocoacylaminoethylhydroxyethylcarboxymethyl glycinate. A preferred zwitterionic surfactant is the fatty acid amide derivative known by the CTFA name cocamidopropyl betaine.

Ampholytic surfactants are to be understood as meaning surface-active compounds that, in addition to a $C_8-C_{18}$-alkyl or -acyl group, contain at least one free amino group and at least one $-COOH$ or $-SO_3H$ group in the molecule and are capable of forming internal salts. Examples of suitable ampholytic surfactants include N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids, each having approximately from 8 to 18 carbon atoms in the alkyl group. Ampholytic surfactants to which special preference is given are N-cocoalkylaminopropionate, cocoacylaminoethylaminopropionate and $C_{12}-C_{18}$ acylsarcosine.

Non-ionic surfactants contain as the hydrophilic group, for example, a polyol group, a polyalkylene glycol ether group or a combination of polyol and polyglycol ether groups.

Such compounds are, for example:

addition products of from 2 to 30 mol of ethylene oxide and/or from 0 to 5 mol of propylene oxide with linear fatty alcohols having from 8 to 22 carbon atoms, with fatty acids having from 12 to 22 carbon atoms and with alkylphenols having from 8 to 15 carbon atoms in the alkyl group, $C_{12}-C_{22}$ fatty acid mono- and di-esters of addition products of from 1 to 30 mol of ethylene oxide with glycerol, $C_6-C_{22}$ alkyl-mono- and -oligo-glycosides and ethoxylated analogues thereof, addition products of from 5 to 60 mol of ethylene oxide with castor oil and hydrogenated castor oil, addition products of ethylene oxide with sorbitan fatty acid esters, addition products of ethylene oxide with fatty acid alkanolamides.

Examples of cationic surfactants that can be used in the hair-treatment compositions according to the invention are especially quaternary ammonium compounds. Preference is given to ammonium halides, such as alkyltrimethylammonium chlorides, dialkyldimethylammonium chlorides and trialkylmethylammonium chlorides, for example cetyltrimethylammonium chloride, stearyltrimethylammonium chloride, distearyldimethylammonium chloride, lauryldimethylammonium chloride, lauryldimethylbenzylammonium chloride and tricetylmethylammonium chloride. Further cationic surfactants that can be used in accordance with the invention are quaternised protein hydrolysates.

Also suitable in accordance with the invention are cationic silicone oils, such as, for example, the commercially available products Q2-7224 (manufacturer: Dow Corning; a stabilised trimethylsilylamodimethicone), Dow Corning 929 emulsion (comprising a hydroxylamino-modified silicone, which is also referred to as amodimethicone), SM-2059 (manufacturer: General Electric), SLM-55067 (manufacturer: Wacker) and also Abil®-Quat 3270 and 3272 (manufacturer: Th. Goldschmidt; diquaternary polydimethylsiloxanes, quatemium-80).

Alkylamidoamines, especially fatty acid amidoamines, such as the stearylamidopropyl-dimethylamine obtainable under the name Tego Amid® 18, are distinguished not only by a good conditioning action but also especially by their good biodegradability.

Quaternary ester compounds, so-called "esterquats", such as the methyl hydroxyalkyldialkoyloxyalkylammonium methosuliates marketed under the trade mark Stepantex®, are also very readily biodegradable.

An example of a quaternary sugar derivative that can be used as cationic surfactant is the commercial product Glucquat®100, according to CTFA nomenclature a "lauryl methyl gluceth-10 hydroxypropyl dimonium chloride".

The alkyl-group-containing compounds used as surfactants may be single substances, but the use as starting materials of natural raw materials of vegetable or animal origin is generally preferred in the preparation of such substances, with the result that the substance mixtures obtained have different alkyl chain lengths according to the particular starting material used.

The surfactants that are addition products of ethylene oxide and/or propylene oxide with fatty alcohols or derivatives of such addition products may either be products having a "normal" homologue distribution or products having a restricted homologue distribution. "Normal" homologue distribution is to be understood as meaning mixtures of homologues obtained in the reaction of fatty alcohol and alkylene oxide using alkali metals, alkali metal hydroxides or alkali metal alcoholates as catalysts. Restricted homologue distributions, on the other hand, are obtained when, for example, hydrotalcites, alkali metal salts of ether carboxylic acids, alkali metal oxides, hydroxides or alcoholates are used as catalysts. The use of products having restricted homologue distribution may be preferred.

Examples of further active ingredients, adjuvants and additives are as follows:

non-ionic polymers, for example vinylpyrrolidone/vinyl acrylate copolymers, polyvinylpyrrolidone and vinylpyrrolidone/vinyl acetate copolymers and polysiloxanes, cationic polymers, such as quaternised cellulose ethers, polysiloxanes having quaternary groups, dimethydiallylammonium chloride polymers, copolymers of dimethyldiallylammonium chloride and acrylic acid, as available commercially under the name Merquat$^R$ 280 and the use of which in hair dyeing is described, for example, in DE-A-4 421 031, especially page 2, lines 20 to 49, or EP-A-953 334, especially page 27, line 17 to page 30, line 11, acrylamide/dimethyldiallylammonium chloride copolymers, diethyl-sulfate-uaternised dimethylaminoethyl methacrylate/vinylpyrrolidone copolymers, vinylpyrrolidone imidazolinium methochloride copolymers, quaternised polyvinyl alcohol, zwitterionic and amphoteric polymers, such as, for example, acrylamidopropyl-trimethyl-ammonium chloride/acrylate copolymers and octylacrylamide/methyl methacrylate/tert-butylaminoethyl methacrylate/2-hydroxypropyl methacrylate copolymers, anionic polymers, such as, for example, polyacrylic acids, crosslinked polyacrylic acids, vinyl acetate/crotonic acid copolymers, vinylpyrrolidone/vinyl acrylate copolymers, vinyl acetate/butyl maleate/isobomyl acrylate copolymers, methyl vinyl ether/maleic anhydride copolymers and acrylic acidlethyl acrylate/N-tert-butyl acrylamide terpolymers, thickeners, such as agar, guar gum, alginates, xanthan gum, gum arabic, karaya gum, locust bean flour, linseed gums, dextrans, cellulose derivatives, e.g. methyl cellulose, hydroxyalkyl cellulose, hydroxyethyl ethylcellulose and carboxymethyl cellulose, starch fractions and derivatives, such as amylose, amylopectin and dextrins, clays, e.g. bentonite or fully synthetic hydrocolloids such as, for example, polyvinyl alcohol, structuring agents, such as glucose and maleic acid, hair-conditioning compounds, such as phospholipids, for example soya lecithin, egg lecithin, and cephalins, silicone oils, and also conditioning compounds, for example such as those described in DE-A-1 9 729 080, especially page 2, lines 20 to 49, EP-A-834 303, especially page 2, line 18 to page 3, line 2, or EP-A-312 343, especially page 2, line 59 to page 3, line 11, protein hydrolysates, especially elastin, collagen, keratin, milk protein, soya protein and wheat protein hydrolysates, condensation products thereof with fatty acids and also quatemised protein hydrolysates, and phospholipids, like ceramide, perfume oils, dimethyl isosorbitol and cyclodextrins, solubilisers, such as ethanol, isopropanol, ethylene glycol, propylene glycol, glycerol and diethylene glycol, anti-dandruff active ingredients, such as piroctones, olamines and zinc Omadine, further substances for adjusting the pH value, active ingredients such as panthenol, pantothenic acid, allantoin, pyrrolidonecarboxylic acids and salts thereof, plant extracts and vitamins, cholesterol, light stabilisers and UV absorbers, as described, for example, in EP-A-819 422, especially page 4, lines 34 to 37, and WO-A-01/36396, especially the compounds on pages 4 and 5, consistency regulators, such as sugar esters, polyol esters or polyol alkyl ethers, fats and waxes, such as spermaceti, beeswax, montan wax, paraffins, fatty alcohols and fatty acid esters, fatty acid alkanolamides, polyethylene glycols and polypropylene glycols having a molecular weight of from 150 to 50 000, for example such as those described in EP-A-801 942, especially page 3, lines 44 to 55, complexing agents, such as EDTA, NTA and phosphonic acids, swelling and penetration substances, such as polyols and polyol ethers, as listed extensively, for example, in EP-A-962 219, especially page 27, lines 18 to 38, for example glycerol, propylene glycol, propylene glycol monoethyl ether, butyl glycol, benzyl alcohol, carbonates, hydrogen carbonates, guanidines, ureas and also primary, secondary and tertiary phosphates, imidazoles, tannins, pyrrole, opacifiers, such as latex, pearlising agents, such as ethylene glycol mono- and di-stearate, propellants, such as propane-butane mixtures, $N_2O$, dimethyl ether, $CO_2$ and air, and also antioxidants.

The constituents of the aqueous carrier are used in the preparation of the dyeing compositions according to the invention in the amounts customary for that purpose; for example emulsifiers are used in concentrations of from 0.5 to 30% by weight and thickeners in concentrations of from 0.1 to 25% by weight of the total dyeing composition.

The pH value of the ready-to-use dyeing preparations is usually from 2 to 11, preferably from 5 to 10.

To dye keratin-containing fibres, especially to dye human hair, the dyeing compositions are usually applied to the hair in an amount of from 50 to 100 g in the form of a mixture with the aqueous cosmetic carrier, left on the hair for approximately 30 minutes and then rinsed off or washed off with a commercially available hair shampoo.

The compounds used according to the invention and, where used, the oxidation dye precursors may be applied to the keratin-containing fibres either simultaneously or in succession, the order in which they are applied being unimportant.

The compounds used according to the invention and, where used, the oxidation dye precursors of the compositions according to the invention may be stored separately or together, either in a liquid to paste-like preparation (aqueous or non-aqueous) or in the form of a dry powder. When the components are stored together in a liquid preparation, the preparation should be substantially anhydrous in order to reduce reaction of the components. When they are stored separately, the reactive components are intimately mixed with one another only immediately before use. In the case of dry storage, before use a defined amount of hot (from 50 to 80° C.) water is usually added and a homogeneous mixture prepared.

The following Examples serve to illustrate the invention without limiting the invention thereto. Unless specified otherwise, parts and percentages relate to weight.

APPLICATION EXAMPLE 1

A strongly alkaline 10% solution of a non-ionic surfactant (Plantaren 2000, Henkel) is adjusted to pH 9.5 using citric acid. 0.1% of the dye of formula

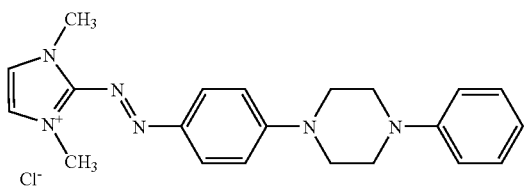

is dissolved therein and a strand of human hair, bleached white, is treated with the dye solution at room temperature. After only a short period of time, the strand has been dyed a red shade, which is still very intense even after shampooing ten times. The dye also has a strong affinity for undamaged hair. In that case, too, the fastness to washing is very good.

APPLICATION EXAMPLE 2

A 0.1% solution of the dye according to the invention of formula

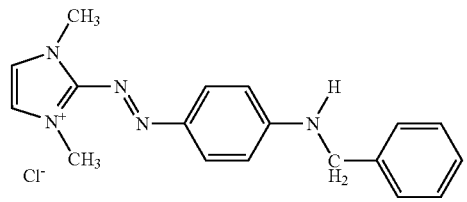

in a surfactant base consisting of 10% cocoamphoglycinate and 90% water is applied for 20 minutes to a strand each of bleached and unbleached white human hair ("Italian white virgin" IMHAIR Ltd.), rinsed and shampooed once. Very intense, vibrant scarlet dyeings of identical shade are obtained on both qualities of hair. Surprisingly, both the colour strength and fastness to washing are excellent and very similar for both qualities of hair, which speaks for the good levelling ability of this product.

APPLICATION EXAMPLE 3

A dye emulsion, containing 0.1% of the dye according to the invention of formula

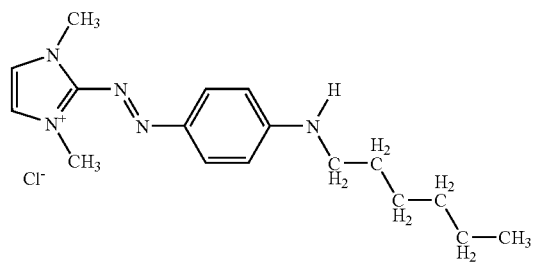

3.5% cetearyl alcohol
1.0% ceteareth 80
0.5% glyceryl mono-di-stearate
3.0% stearamide DEA
1.0% stearamphopropyl sulfonate
0.5% polyquaternium-6 and
water ad 100% is applied for 30 minutes, at room temperature, to bleached human hair, rinsed and shampooed once. The result is a very attractive vibrant red dyeing that has good fastness to washing. A very interesting red dyeing is likewise obtained on undamaged human hair.

APPLICATION EXAMPLE 4

Example 4 illustrates a method for "lightening" dyeings, as described also in WO 97/20545.

The following dye solution is prepared:
1 g of the dye according to the invention from Example 3
10 g of a 20% ammonia solution
water ad 100 g.

The solution is combined with the same weight of a 6% hydrogen peroxide solution and the mixture is immediately applied to a strand of dark-blonde natural European hair. After 5 minutes, the strand of hair is rinsed and dried.

The naturally present melanine is bleached by the hydrogen peroxide, while the dye according to the invention is nearly not affected. It will be understood that this could also be achieved using a two-step process, but one of the important advantages of the dyes according to the invention is that, owing to the extraordinary pH stability thereof, the two steps can be carried out simultaneously, which is not possible with most direct dyes. Similar results are obtained if a dye according to Application Example 1 or 2 is used.

APPLICATION EXAMPLE 5

A dye formulation is prepared from
0.1 g of the dye according to the invention from Example 2
1.0 g of carboxymethyl cellulose ("Blanose 7M", Societe AQUALON)
10 g of ethanol and
water ad 100 g.

The pH of the solution is adjusted to 9 using 2-amino-2-methyl-1-propanol.

The solution is applied for 30 minutes to strands of grey human hair 90% of which is white. A very bright, intense red dyeing is obtained.

Similar results are obtained if a dye of Application Example 1 or 3 is used.

PREPARATION EXAMPLE 1

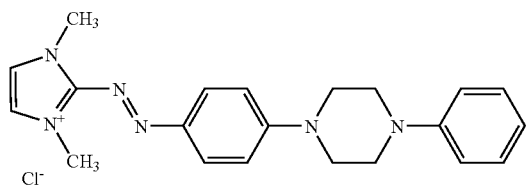

53.2 g of the educt of formula

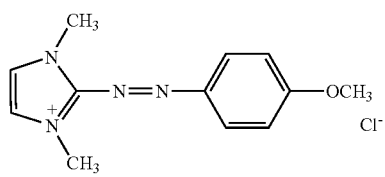

(101)

is slurried in 40 g 2-propanol at room temperature. The temperature is then raised to 45–50° C. and 40 g of N-phenylpiperazine is added. The mixture is stirred for 30 hours. Then the reaction mass is diluted with 140 g of methyl-ethyl-ketone, cooled to room temperature, when crystallization occurs. The crystal suspension is separated by filtration, washed twice with 20 g methyl-ethyl-ketone and dried in a vacuum dryer to get 63 g of a dark powder.

PREPARATION EXAMPLE 2

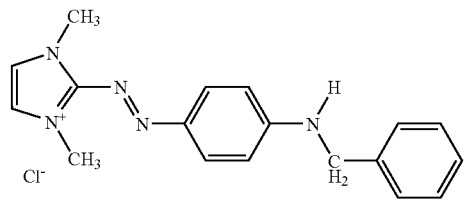

60.6 g of the educt of formula (101) is slurried in 43 g 2-propanol at room temperature. The temperature is then raised to 45–50° C. and 30.3 g of benzyl amine is added. The mixture is stirred for 20 hours for the completion of reaction. Then the reaction mass is diluted in 0.5 hours with 140 g of methyl-ethyl-ketone, cooled during 3 hours to room temperature, when crystallization occurs. The crystal suspension is separated by filtration, washed twice with 20 g methyl-ethyl-ketone, then with 20 g 2-propanol and dried under vacuum to get 53 g of a dark powder.

PREPARATION EXAMPLE 3

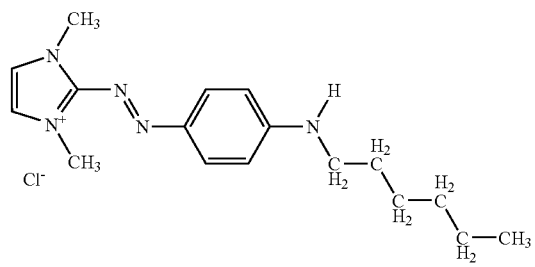

60 g of the educt of formula (101) is slurried in 45 g 2-propanol at room temperature. The temperature is then raised to 45–50° C. and 20 g of n-hexylamine is added. The mixture is stirred for 17 hours. Then the reaction mass is diluted with 140 g of methyl-ethylketone, cooled during 3 hours to room temperature, when crystallization occurs. The crystal suspension is separated by filtration, washed twice with 20 g methyl-ethylketone and dried at vacuum to get ca. 50 g of a dark powder.

What is claimed is:

1. A method of dyeing fibres of living human hair, which comprises contacting the fibres with a dye of the formula

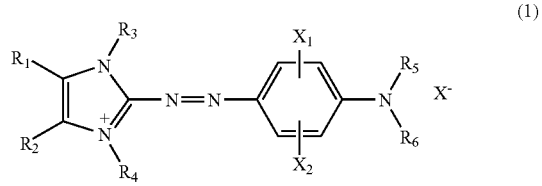

(1)

wherein
$R_1$ and $R_2$ are each independently of the other hydrogen, $C_1$–$C_4$alkyl, halogen or nitro, $R_3$ and $R_4$ are each independently of the other unsubstituted $C_1$–$C_4$alkyl or $C_1$–$C_4$alkyl substituted by OH, $C_1$–$C_4$alkoxy, halogen, CN or by phenyl, $X_1$ and $X_2$ are each independently of the other hydrogen, $C_1$–$C_4$alkyl, $C_1$–$C_4$alkoxy or halogen, $R_5$ is hydrogen or $C_1$–$C_4$alkyl, $R_6$ is $C_5$–$C_8$cycloalkyl each unsubstituted or substituted by OH, $C_1$–$C_4$alkoxy, halogen, CN or phenyl, or $R_6$ is $C_1$–$C_4$alkyl substituted by phenyl or by $C_5$–$C_8$cycloalkyl, or wherein $R_5$ and $R_6$ together with the nitrogen atom linking them form a piperazine ring, which is substituted, at the nitrogen atom that is not bonded to the phenyl group, by phenyl, or which is quaternised at that nitrogen atom by two penyl groups, the phenyl mentioned as substituents of the nitrogen atom of the piperazine ring being unsubstituted or substituted by OH, $C_1$–$C_4$alkoxy, halogen, CN or phenyl, and wherein $X^-$ is an anion.

2. A method according to claim 1, which comprises contacting the fibres with a dye of formula (1) wherein each of $R_1$ and $R_2$ is methyl or hydrogen.

3. A method according to claim 1, which comprises contacting the fibres with a dye of formula (1) wherein each of $R_3$ and $R_4$ is ethyl, hydroxyethyl or methyl.

4. A method according to claim 1, which comprises contacting the fibres with a dye of formula (1) wherein each of $X_1$ and $X_2$ is methoxy, methyl, hydrogen or chlorine.

5. A method according to claim 1, which comprises contacting the fibres with a dye of formula

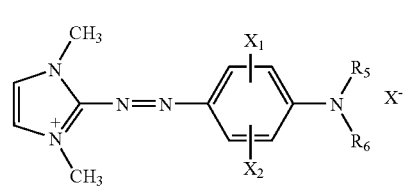

(2)

wherein
$X_1$ and $X_2$ are each independently of the other hydrogen, methyl or methoxy,
$R_5$ is hydrogen,
$R_6$ is benzyl, or cyclohexyl,
or wherein $R_5$ and $R_6$ together with the nitrogen atom linking them form a piperazine ring, which is substituted, at the nitrogen atom that is not bonded to the phenyl ring, by phenyl, and
$X^-$ is an anion.

6. A method according to claim 5, wherein $R_6$ is benzyl, or cyclohexyl.

7. A method according to claim 6, wherein $R_6$ is benzyl.

8. A method according to claim 6, wherein $R_6$ is cyclohexyl.

9. A composition which dyes living human hair, comprising at least one dye of formula (1) according to claim 1 and a cosmetically acceptable carrier.

* * * * *